(12) United States Patent
Lahm et al.

(10) Patent No.: US 7,797,030 B2
(45) Date of Patent: Sep. 14, 2010

(54) CLINICAL TOOL FOR STRUCTURE LOCALIZATION

(75) Inventors: Ryan P. Lahm, Blaine, MN (US); Walton W. Baxter, III, San Clemente, CA (US); Josee Morissette, Eden Prairie, MN (US); Timothy G. Laske, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 1706 days.

(21) Appl. No.: 10/987,815

(22) Filed: Nov. 12, 2004

(65) Prior Publication Data

US 2005/0148850 A1 Jul. 7, 2005

Related U.S. Application Data

(60) Provisional application No. 60/520,358, filed on Nov. 13, 2003.

(51) Int. Cl.
*A61B 5/05* (2006.01)
*G06K 9/00* (2006.01)

(52) U.S. Cl. .................. 600/407; 382/128; 600/414

(58) Field of Classification Search .............. 382/128, 382/131; 600/414, 424; 33/1 A, 20.4; 702/150, 702/94

See application file for complete search history.

(56) References Cited

U.S. PATENT DOCUMENTS

| 5,608,849 A | * | 3/1997 | King, Jr. ................. 345/419 |
| 6,584,339 B2 | | 6/2003 | Galloway, Jr. et al. ....... 600/426 |
| 7,338,449 B2 | * | 3/2008 | Gueck et al. ............. 600/447 |

FOREIGN PATENT DOCUMENTS

| WO | 94/24631 A | 10/1994 |
| WO | 03/070102 A | 8/2003 |

\* cited by examiner

*Primary Examiner*—Eric F Winakur
*Assistant Examiner*—Helene Bor

(57) ABSTRACT

A method for localizing an internal body structure during an image-guided procedure that includes obtaining a three dimensional image of a body portion containing a targeted structure and selected reference structures; determining a set of landmark point coordinates for defining the location of each of the targeted and reference structures; computing triangulation parameters relating the location of the landmark points for the targeted structure and the reference structures; and, during an image-guided procedure, using the computed triangulation parameters to plot an estimated location of the targeted structure on an intra-operative image in which the reference structures have been identified.

25 Claims, 9 Drawing Sheets

CLINICAL TOOL FOR STRUCTURE LOCALIZATION

CLAIM OF PRIORITY

This application claims priority from provisional Application Ser. No. 60/520,358, filed Nov. 13, 2003, entitled "CLINICAL TOOL FOR STRUCTURE LOCATION."

FIELD OF THE INVENTION

The present invention relates to methods for guiding medical interventions using anatomical or pathological landmarks and more particularly to a data collection and processing method that facilitates image-guided surgery.

BACKGROUND OF THE INVENTION

Minimally invasive techniques are being developed for a variety of surgical procedures. During such procedures, the clinician typically relies on intra-operative imaging to guide instrumentation to a targeted therapy or diagnostic site. This maneuvering is often the most time-consuming portion of the procedure as it can require considerable skill and intuition, particularly when the intra-operative images are two-dimensional images. With the increasing use of minimally invasive techniques, clinical tools are needed that aid a clinician in quickly and accurately localizing a targeted site during a surgical procedure.

BRIEF SUMMARY OF THE INVENTION

The invention provides a method for aiding a clinician in localizing a structure within a patient's body during a medical intervention. The method generally includes first producing a set of measurements that define the location of a targeted site relative to at least two reference structures or at least one reference structure and a local coordinate system. The set of measurements are then used during a surgical procedure to project an estimated location of the targeted site on an intra-operative image.

Methods provided by the invention include a data acquisition method for obtaining triangulation parameter data performed prior to a surgical procedure and an image-guided localization method for plotting an estimated target structure location on an intra-operative image using the previously obtained triangulation parameter data. The data acquisition method includes: forming a spatially accurate 3D image volume of a body portion wherein a targeted structure for a surgical procedure is located within the volume; selecting structure(s) within the image volume to serve as reference structures for use in localizing the targeted structure; determining landmark point coordinates defining the location of each of the targeted and reference structures within the volume; and computing triangulation parameter data relating the locations of the landmark points.

The localization method performed during a surgical procedure includes locating the reference structures on a medical image obtained intra-operatively, and plotting an estimated location of the targeted structure on the intra-operative image using the computed triangulation parameter data and the identified reference structure locations.

In embodiments utilizing 3D imaging during the surgical procedure, the triangulation parameters determined previously based on landmark point coordinates in three dimensions are used to plot the estimated location of the targeted structure on a 3D intra-operative image, wherein the locations of the reference structures have been identified.

In embodiments utilizing 2D imaging during the surgical procedure, the method for producing the triangulation parameter data further includes: calculating an isocenter of the body portion and rotating the landmark points about an isocenter axis to a given angle corresponding to a selected 2D planar view; projecting the landmark points onto the selected plane; and calculating triangulation parameters relating the locations of the projected landmark point coordinates. During a surgical procedure, the estimated location of the targeted structure is plotted on the selected 2D planar image obtained intra-operatively. The plotted location is based on the projected triangulation parameter data and identified locations of reference structures in the 2D intra-operative image.

In some embodiments, a single reference structure and the local coordinate system are used in conjunction with a targeted structure for determining a set of localization parameters in a 2D imaging plane. The targeted structure is plotted on an intra-operative image based on the identified location of the reference structure and localization parameters relating the location of the reference structure, targeted structure and a local coordinate system axis.

DETAILED DESCRIPTION

The invention provides clinicians with a useful tool for localizing internal structures particularly during minimally invasive procedures during which the clinician does not have direct line of sight view of a targeted structure. The targeted structure may be an anatomical structure, a pathological feature, or an implanted device. During a minimally invasive procedure, the clinician is typically guiding an instrument or medical device toward the targeted structure by viewing the position of the instrument in a 2D or 3D image obtained intra-operatively. Such procedures can be time-consuming and require considerable skill and intuition. The invention provides a method for plotting an estimated location of a targeted structure on intra-operative medical images to aid the clinician in localizing the targeted structure. The plotted location is estimated based on previously collected triangulation parameter data relating the targeted structure location to selected reference structures. The triangulation data can be determined from three-dimensional images of the patient undergoing the procedure or from another subject or population of subjects.

Methods provided by the present invention include a prospective data acquisition method and a localization method for use during a surgical procedure. The data acquisition method is performed for determining triangulation parameters relating the location of a structure targeted for a surgical procedure to the locations of selected reference structures. The triangulation parameters are later applied during the surgical procedure in a localization method for guiding an instrument to the targeted structure. The localization method may be performed using either 3D or 2D intra-operative imaging. The data acquisition method is performed using 3D imaging and the steps performed will depend on whether 3D or 2D intra-operative images are used during the surgical procedure. In the description that follows, the data acquisition method and localization method for 3D image-guided localization applications are described in conjunction with FIGS. 1 through 3B. The data acquisition method and localization methods for 2D image-guided localization applications are described in conjunction with FIGS. 4 through 8.

Figure 1:
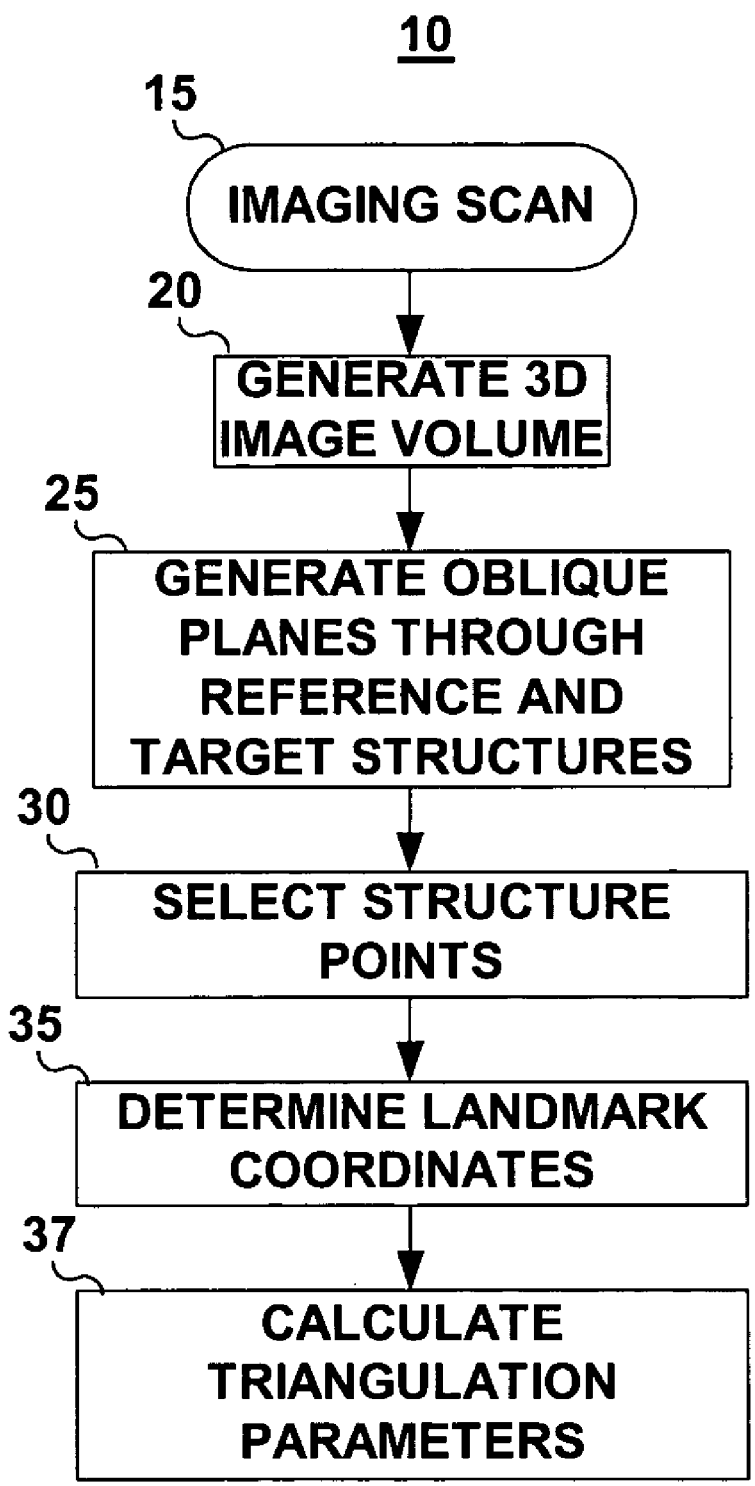
FIG. 1 is a flow chart summarizing steps included in a data acquisition method for computing triangulation parameter data relating reference structure and targeted structure locations in three dimensions.

FIG. 1 is a flow chart summarizing steps included in a data acquisition method for computing triangulation parameter data relating reference structure and targeted structure locations in three dimensions. Triangulation parameter data acquired using method 10 of FIG. 1 will be used later in an image-guided procedure utilizing 3D intra-operative medical images. Based on the acquired triangulation parameter data, a targeted site location will be plotted in a 3D volume defined by three dimensional medical images obtained during a surgical procedure. Intra-operative images are typically obtained using fluoroscopy but could be obtained using any available medical imaging technology such as ultrasonography.

In step 15 of data acquisition method 10, volumetric medical images from patients or volunteers are collected, using any type of imaging method that exists, examples of which include, but are not limited to, computed tomography (CT) and magnetic resonance imaging (MRI). In some applications, images are time-gated images to reduce physiological motion artifact from triangulation measurements. Images may be gated to a particular time point in the respiration and/or cardiac cycle to reduce the effects of respiratory and cardiac motion on the triangulation parameter measurements.

Once a series of volumetric images have been obtained, the images are stacked to form a spatially accurate 3D image volume at step 20. Analyze, a biomedical image analysis software package developed at the Mayo Clinic in Rochester, Minn. and distributed by AnalyzeDirect, may be used to perform step 20. The image volume obtained at step 20 serves as a virtual representation of the true anatomy found in the patient or volunteer from which the images were acquired. The image volume is acquired so as to contain the targeted structure and selected reference structures. At least three reference structures are expected to be required for generating a set of triangulation parameter data that may be used for plotting the location of a targeted structured on a 3D intra-operative image.

The reference structures may be selected as structures that are generally more readily located and identified on a medical image than the targeted structure. Low variability in the anatomical locations of the selected reference structures, relative to each other and to the targeted structure, will promote greater accuracy in plotting the estimated location of the targeted structure during a surgical procedure. In this data acquisition phase, multiple reference points may be initially selected, with some points later rejected due to high anatomical variation causing undesirable variability in the triangulation parameters.

Reference structures are not restricted to anatomical structures. Implanted devices may be selected as reference structures. Implantable devices may already be present in the patient's body such as a pacemaker, drug pump, leads, orthopedic implants, or other devices. Implantable devices may be placed for the purpose of serving as reference structures during an image guided procedure. For example, a catheter tip or other type of marker may be positioned at a desired location to serve as a reference structure.

As noted previously, the targeted structure may be an anatomical structure, pathological feature, or an implanted device. A medical intervention may be performed to ablate tissue, remove tissue, deliver a drug or biologic material, implant a new medical device, remove, reposition or otherwise alter or adjust an existing implanted medical device, or perform other procedures at a targeted site.

Steps 25 through 35 are directed toward defining landmark point coordinates defining the locations of each of the reference structures and the targeted structure. Numerous methods may be utilized for defining a landmark point for each respective structure. In one embodiment, the user may simply select a point in the medical image corresponding to the structure using a pointing tool. The coordinates of the selected point would then be defined as the landmark point coordinates for that structure. The selected point may be an identifiable aspect of the structure, which is selectable in a reproducible manner in order to promote accuracy of the plotted targeted structure location during a surgical procedure. A landmark point may alternatively be selected using automated techniques that identify a point on the structure in a digitized gray-scale or color image.

In another embodiment, and as shown in FIG. 1, landmark point coordinates may be determined by first generating an oblique plane, through the 3D image volume, containing the structure for which a landmark point is being determined. The "Oblique Sections" module found within the Analyze software package may be used to perform this step. One plane is generated through the targeted structure. Additional planes are generated through each of the selected reference structures. In one illustrative application, triangulation parameter data acquisition for a procedure requiring cannulation of the coronary sinus ostium (CSos) could include generating a plane through the targeted CSos and generating planes through two reference structures which may be selected, for example, as the superior vena cava (SVC) ostium and the tricuspid valve (TV) annulus.

The oblique planes are generated through the 3D volume such that each plane best represents a 2D profile of each respective targeted and reference structures. In the example given above, an SVC ostium plane would be generated to include a perimeter of the SVC where the SVC enters into the right atrium. A TV annulus plane would be generated to include a perimeter of the valve at the interface between the right atrium and the right ventricle, and the CSos plane would be generated to include a perimeter of the CSos along a wall of the right atrium.

Once a plane has been generated for the targeted structure and each of the reference structures, points that define the associated structure are selected in step 30. In one embodiment, points along a boundary of each structure may be manually selected using a pointing tool. In other embodiments, point selection may be automated. For example, points may be automatically selected based on boundary detection of digitized gray-scale or color images.

A point-picking tool within the "Oblique Sections" module of the Analyze software may be used to perform step 30 and each set of boundary points or border coordinates selected can be saved to a text file.

In step 35, landmark point coordinates are determined for each reference structure and the targeted structure. In the embodiment shown in FIG. 1, the landmark point coordinates for a given structure are determined from one or more of the points selected in step 30. The landmark point coordinates define the location of the associated structure in the imaging volume. In one embodiment, the landmark point may be a centroid calculated from points selected along the border or perimeter of the structure. The landmark coordinates may be calculated using commercially available software, such as Matlab software (The Mathworks, Natick, Mass.). A simple Matlab script developed by the inventors, called "centroid.m", takes scaled sets of selected boundary point coordinates and calculates an average location of these points, otherwise known as the centroid.

In step 37, triangulation parameters are determined for the landmark point coordinate sets determined at step 35 corresponding to a targeted structure landmark point and the selected reference structure landmark points. Distances between the reference structure landmark points and distances between reference structure landmark points and the targeted structure landmark point are determined. Distance ratios relating the distance between a reference structure and the targeted structure to the distance between two reference structures are then determined. By utilizing ratios of distance measurements, the spatial relation of the structures can be estimated regardless of measuring units or body size.

Angles between line segments extending between the landmark points are also determined in step 37. Using the computed distance ratios and angles, the location of the targeted structure can be estimated and plotted in an image in which the locations of the reference structures are known.

The same Matlab script used for calculating a centroid developed by the inventors can be used to calculate the distances between each of the landmark points. These distances define the length of each leg of a triangle defined by the landmark points of the targeted structure and two reference structures. Ratios of the calculated distances and the angles between each of the three vector pairs formed by a triangle of landmark points can be determined. In one embodiment, the triangulation parameters determined at step 37 include at least two distance ratios and two angles determined from two different triangles that each include two reference landmark points and the targeted landmark point.

Method 10 could be performed in a patient-specific manner wherein method 10 is performed prospectively on a patient due to undergo a procedure. Triangulation parameters determined previously for the patient, are applied during the procedure to plot the estimated location of the targeted structure on an intra-operative image acquired, in which the reference structure locations have been identified.

Method 10 can be performed in a number of subjects selected from a population such that representative triangulation parameters for a set of reference and targeted structures can be determined. Triangulation parameters having a low variability in a population of patients can be used to help localize a targeted structure in a given patient undergoing an image-guided procedure. Triangulation parameters determined in a number of subjects may be statistically analyzed to determine a representative set of triangulation parameters. For example, mean values for triangulation parameters may be determined. Triangulation parameter data obtained from a population of patients can be available immediately for use in emergency procedures when time does not allow for prospective, data-gathering imaging procedures to be performed in a patient specific manner.

Figure 2A:
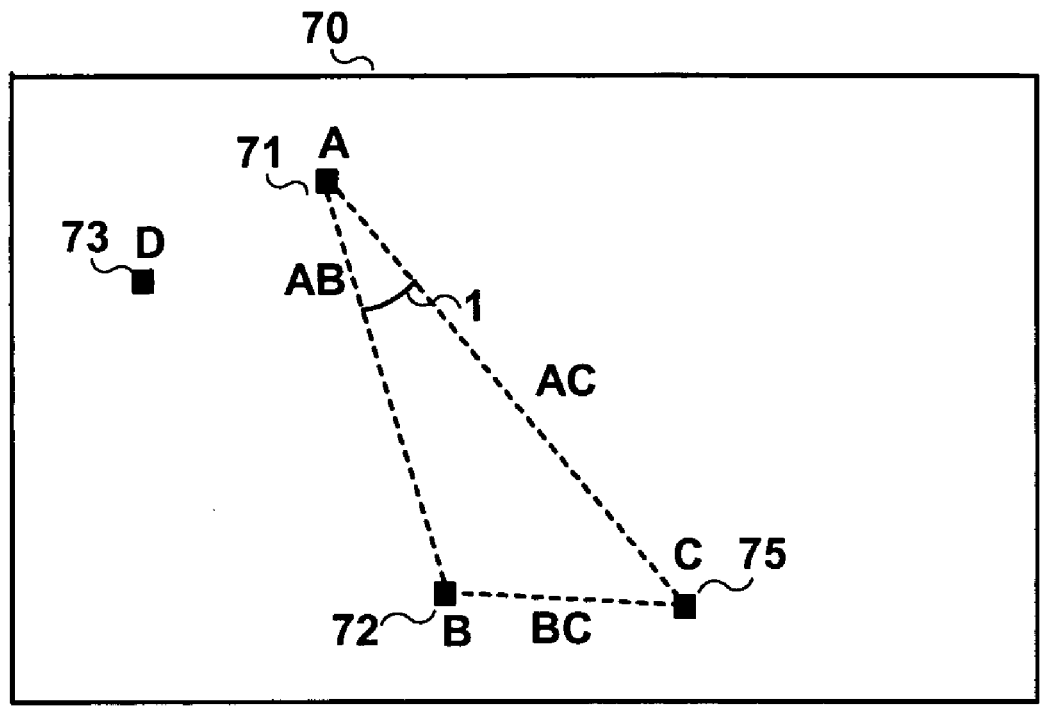
FIGS. 2A and 2B illustrate a set of triangulation parameters that may be computed during the data acquisition method shown in FIG. 1.
Figure 2B:
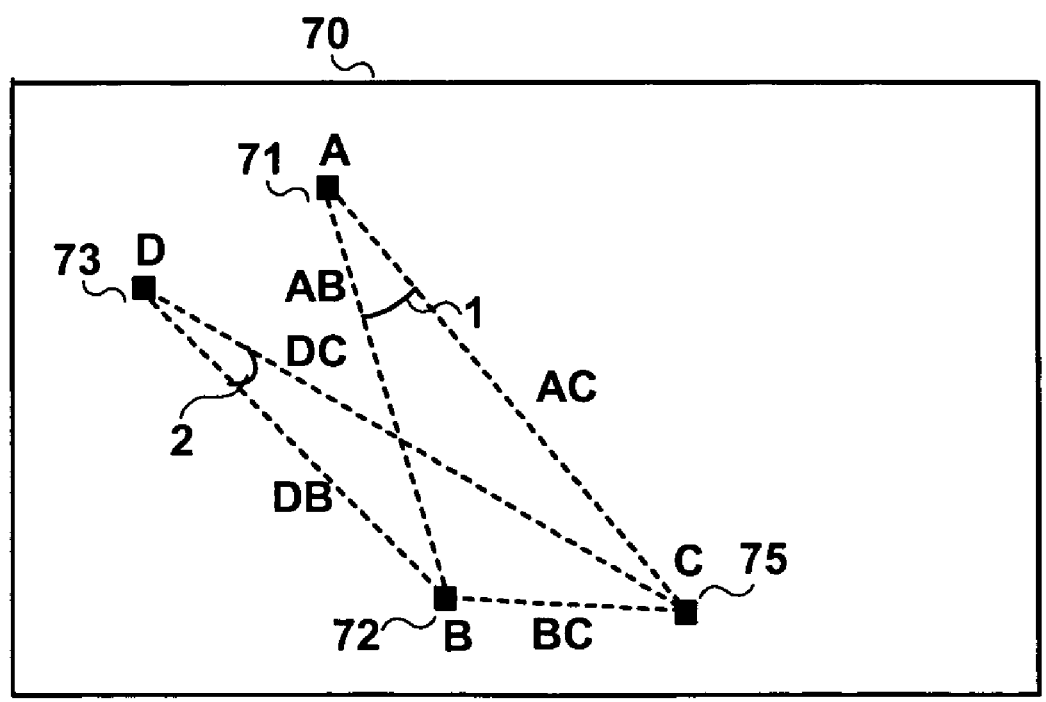

FIGS. 2A and 2B illustrate a set of triangulation parameters that may be computed during data acquisition method 10 (FIG. 1). These parameters will be used in a localization method during an image-guided surgical procedure utilizing 3D intra-operative images. It is expected that at least three reference points will generally be required for determining triangulation parameters that allow a targeted structure location to be plotted in a 3D intra-operative image. In FIG. 2A, three reference landmark points 71, 72, and 73 and a targeted structure landmark point 75 have been identified. A triangle ABC is formed by two reference landmark points 71 and 72 and the targeted landmark point 75. A set of triangulation parameters determined from triangle ABC will include one distance ratio and one angle. The distance ratio will be the ratio of the distance between either of the reference landmark points 71 or 72 and the targeted landmark point 75 to the distance between the two reference landmark points 71 and 72. For example, the distances AC and AB may be determined for computing the distance ratio AC:AB from the landmark point coordinates. The angle enclosed by the sides of the triangle AC and AB, angle 1 is also computed from the landmark point coordinates.

In FIG. 2B, a second set of triangulation parameters are determined from the triangle DBC formed by the third reference landmark point 73, landmark point 72, and targeted landmark point 75. The second set of triangulation parameters also includes distance ratio and an angle determined from triangle DBC. For example the distance ratio DC:DB and the angle 2 may be computed from the landmark point coordinates.

Additional reference structures may be selected to improve the accuracy of a plotted targeted point location. In some three-dimensional applications, triangulation parameters may be collected for more than two triangles formed when more than three reference structures are selected. When three landmark points are identified for three reference structures, two sets of triangulation parameters, each including one distance ratio and one angle, are determined for the two triangles formed by the three reference landmark points and the targeted landmark point. In other embodiments, additional triangulation parameters may be determined from triangles formed using four or more reference structure landmark points and the targeted structure landmark point. By increasing the number of reference structures used for obtaining a set of triangulation data, the error in predicting a targeted site location may be minimized. More time may be required during an invasive procedure for identifying additional reference structures in an intra-operative image, but the targeted site location may be predicted more precisely, reducing overall procedure time.

Other techniques for locating reference or targeted structures may be relied upon during 3D imaging procedures. For example, electrophysiological measurements may be performed to aid in locating electrophysiological structures in the heart. In another example application of the present invention, the localization methods described herein may be used to guide a clinician in placing a pacing electrode at the His bundle. Data gathering procedures that rely on 3D imaging and electrophysiological mapping may be used in obtaining the triangulation parameters needed to relate the location of the His bundle to selected reference structures. Electrophysiological measurements would be used to confirm the location of the His bundle.

Figure 3A:
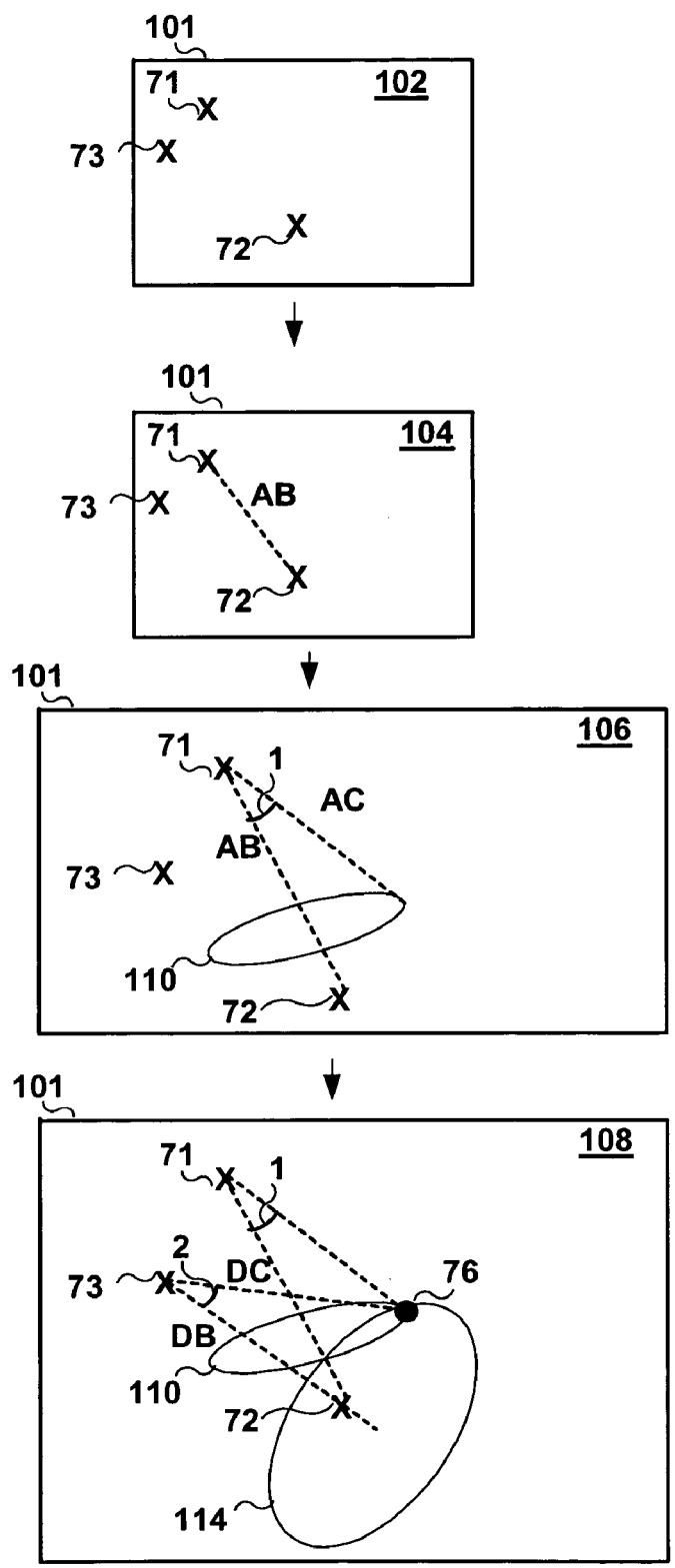
FIG. 3A is an illustration of steps included in a method for applying three-dimensional triangulation parameters in plotting the estimated targeted structure location in a 3D intra-operative image.

FIG. 3A is an illustration of steps included in a method for applying three-dimensional triangulation parameters in plotting the estimated targeted structure location in a 3D intra-operative image. In some applications, three reference points that are coplanar with the targeted structure can be used to localize a targeted structure. The localization method shown in FIG. 3A illustrates one method for plotting an estimated targeted structure location in a 3D image based on triangulation parameters derived from three coplanar reference points.

In step 102, the location of three reference structures 71, 72, and 73 are marked by a user in an intra-operative image frame 101. Image frame 101 is a 3D image of a volume expected to contain each of the reference structures and the targeted structure. The user may designate the location of reference structures using a pointing tool, touch screen or other user appliance compatible with the imaging system. A user should attempt to mark the location of each reference structure at a point corresponding to the respective landmark point used in obtaining triangulation data to improve accuracy of the plotted targeted structure location. For example, if landmark point coordinates correspond to the centroid of a structure, the clinician should attempt to mark the centroid in image 101.

After marking the reference structure locations 71, 72 and 73, the distance between the reference structures 71 and 72 in the intra-operative image 101 is measured in step 104. Using the labeling convention shown in FIGS. 2A and 2B, the distance measured corresponds to the distance AB of one leg of the triangle ABC formed by the two reference structures 71 and 72 and the targeted structure. The distance AB may be measured in any units since unitless distance ratios will be applied to estimate the location of the targeted structure.

One of several possible ways to visualize the mathematics behind the application of 3D triangulation parameters is to consider circles in space defined by the identified reference point locations and the triangulation parameters. In step 106, triangulation parameters are applied to generate a circle 110. A trajectory is rotated around line segment AB at angle 1 to define circle 110 whose perimeter is located a distance AC from point 71. Distance AC is determined from the previously determined distance ratio AC:AB and the distance AB measured in image 101. Angle 1 is the angle previously determined as described in FIG. 2A.

The targeted landmark point is located on, or approximately on, circle 110. The second set of triangulation parameter data obtained during data acquisition method 10 is used to estimate where on circle 110 the targeted landmark point is located. In step 108, a second circle 114 is generated by rotating a trajectory extending from reference point 73 at an angle 2 from line segment DB. The circumference of circle 114 is located a distance DC from point 73 as determined from previously determined distance ratio DC:DB and the distance DB measured in image 101.

The targeted landmark point 76 is plotted at the point that circles 110 and 114 intersect. Plotted point 76 is displayed on the intra-operative image and provides a target for the clinician to guide an instrument toward during the invasive procedure. Circles 110 and 114 may or may not be displayed; circles shown in FIG. 3A are depicted to illustrate the computations that may be used for identifying the estimated targeted structure point 76.

An area or perimeter surrounding the plotted point 76 may be shaded or outlined on the image display to indicate inherent error or variability in the triangulation parameters. Circles 110 and 114 may be defined by a line thickness that produces an estimated 3D target volume at their point of intersection 76. Error may arise when the locations of reference structures 90, 92 and 93 indicated by a user in image frame 121 do not precisely coincide with the landmark point coordinates used in determining triangulation parameters. When triangulation parameters are determined from a patient population, some inter-individual variability will exist in the measured distance ratios and angles leading to variability in the predicted targeted structure location.

In applications where three reference points and the targeted structure are not coplanar, circles 110 and 114 generated using two sets of triangulation parameters may intersect at more than one point. Sometimes a clinician may be able to logically reject one intersection point as not being located in an anatomically realistic location corresponding to the targeted structure. If three points are not sufficient for localizing the targeted structure, a fourth reference structure may be required to generate yet another circle to determine a unique intersection point that defines the targeted structure location. The estimated targeted structure location would be plotted at the intersection of the three circles generated using three sets of triangulation parameters determined using four reference landmark points.

Figure 3B:
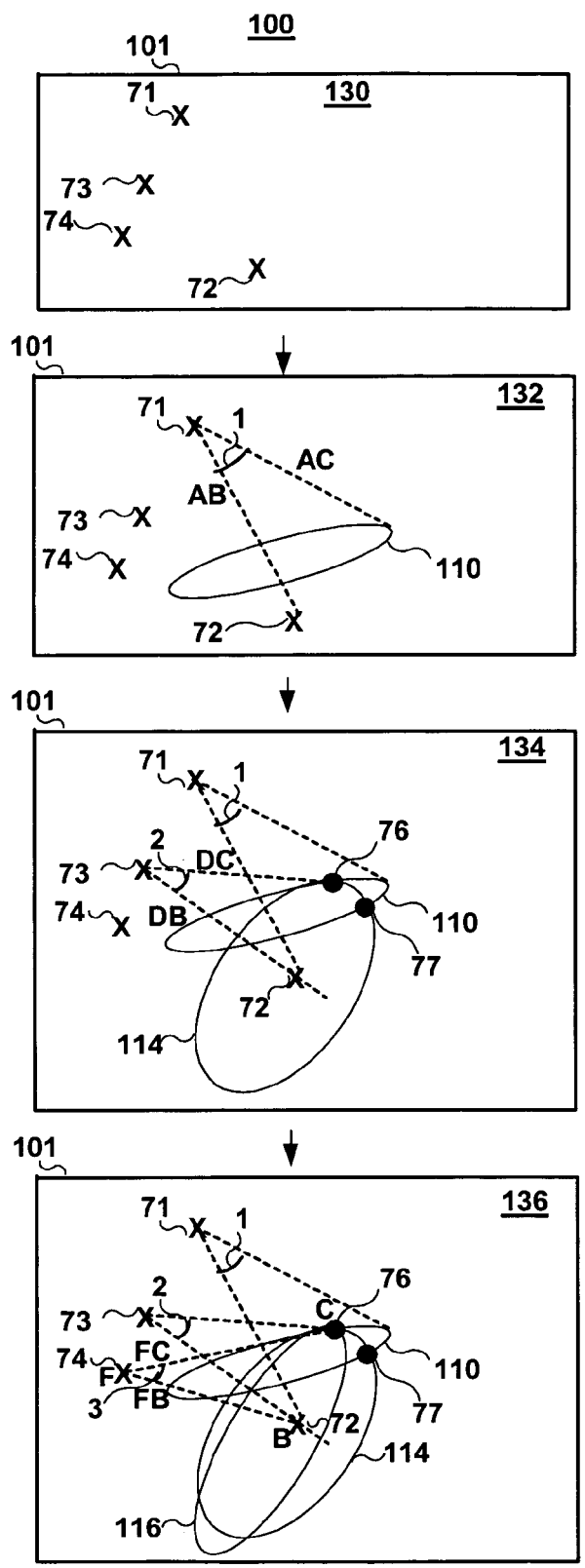
FIG. 3B illustrates the use of four reference landmark points for plotting an estimated targeted structure location in a 3D intra-operative image.

FIG. 3B illustrates the use of four reference landmark points for plotting an estimated targeted structure location in a 3D intra-operative image. In step 130, the location of four reference structures 71, 72, 73, and 74 are marked by a user in an intra-operative image frame 101. Image frame 101 is a 3D image of a volume expected to contain each of the reference structures and the targeted structure.

In step 132, triangulation parameters are applied to generate a circle 110. A trajectory is rotated around line segment AB at angle 1 to define circle 110 whose perimeter is located a distance AC from point 71. Distance AC is determined from the previously determined distance ratio AC:AB and the distance AB measured in image 101. Angle 1 is the angle previously determined as described in FIG. 2A.

The targeted landmark point is located on or approximately on circle 110. The second set of triangulation parameter data obtained during data acquisition method 10 is used to estimate where on circle 110 the targeted landmark point is located. In step 134, a second circle 114 is generated by rotating a trajectory extending from reference point 73 at an angle 2 from line segment DB. The circumference of circle 114 is located a distance DC from point 73 as determined from previously determined distance ratio DC:DB and the distance DB measured in image 102.

In this example, the two reference circles 110 and 114 intersect at two points 76 and 77, one of which is the targeted structure. If the appropriate location of the target cannot be deduced from the two intersecting points, a fourth reference point is needed. Step 136 illustrates the use of a third set of triangulation parameters based on the fourth reference point 74.

The third set of triangulation parameters would include a distance ratio FC:FB and angle 3 corresponding to a third triangle FCB. The third set of triangulation parameters is used to generate a third reference circle 116. Circle 116 is generated by rotating a trajectory extending from fourth reference point 74 at an angle 3 relative to the side FB (extending between reference points 74 and 72) of triangle FCB. The circumference of circle 116 is located a distance FC from reference point 74 as determined by the measured distance FB in image 101 and the previously determined distance ratio FC:FB.

One common intersection point 76 will exist between the three reference circles 110, 114, and 116, defining the targeted structure location. Plotted point 76, displayed on the intra-operative image, provides a target for the clinician to guide an instrument toward during the invasive procedure.

Figure 4:
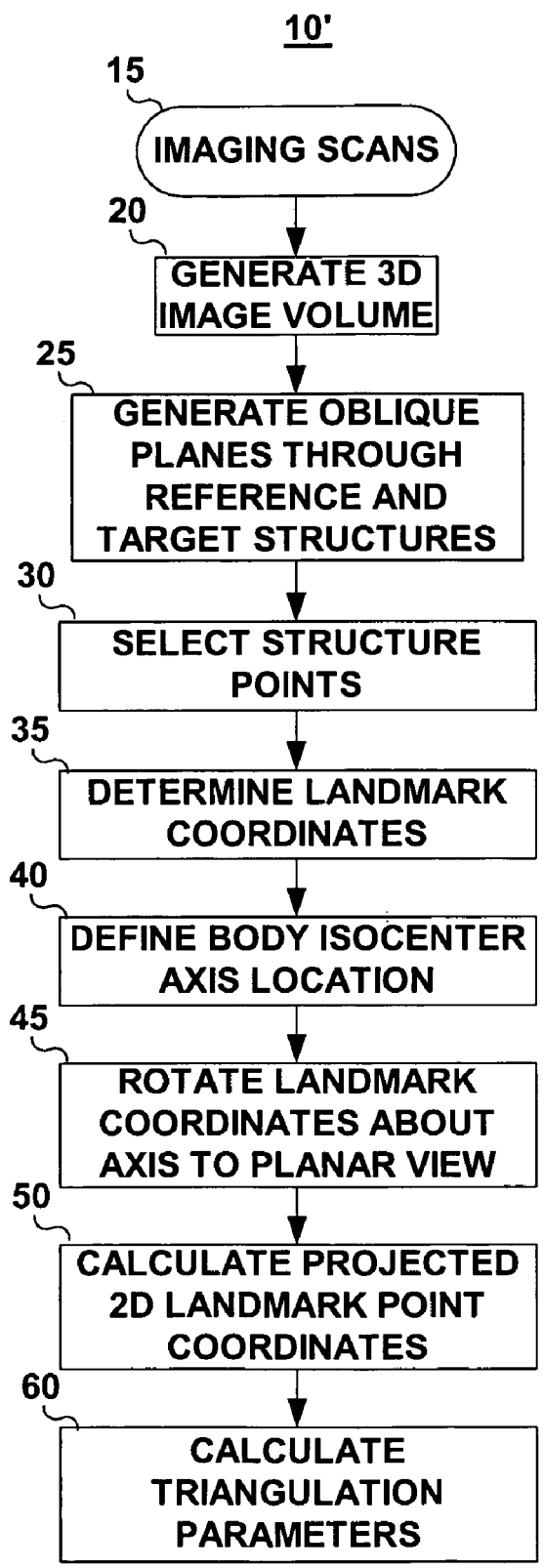
FIG. 4 is a flow chart summarizing steps included in a method for acquiring triangulation parameter measurements for use in two-dimensional image guided surgical procedures.

FIG. 4 is a flow chart summarizing steps included in a method for acquiring triangulation parameter measurements for use in two-dimensional image guided surgical procedures. During an intervention, intra-operative images may be obtained in two or three dimensions. When 3D intra-operative imaging is available, triangulation parameters obtained using method 10 of FIG. 1 maybe applied directly in the intra-operative 3D image as described in conjunction with FIG. 3 above. However, when intra-operative imaging is limited to 2D images, such as 2D fluoroscopy, the three-dimensional landmark coordinates obtained during the data acquisition method need to be projected onto a selected planar view for calculating the triangulation parameters.

Method 10' shown in FIG. 4 includes the steps 15 through 35 as described previously in conjunction with FIG. 1 for determining landmark point coordinates for each of the targeted and reference structures. In 2D image-guided applications, two reference structures are generally expected to be sufficient for use in plotting an estimated targeted structure location. Prior to calculating triangulation parameters at step 60, the landmark points need to be projected onto the two-dimensional planar view that will be used during the planned procedure.

At step 40 of method 10', a location is calculated within the 3D image volume, which is equivalent to an isocenter axis of the patient's body or body region about which a two-dimensional image would be rotated. For example, an isocenter axis of the thoracic cavity may be determined about which a fluoroscopy C-arm would be rotated in a typical invasive procedure guided by 2-D fluoroscopy. The isocenter of the body region may be determined by measuring the height and width of the region in an imaging volume at a designated location. An axis passing through the midway point in each dimension is determined as the isocenter axis. Other methods may be used for determining the location of an isocenter point used to define an isocenter axis about which a 2D imaging plane is rotated.

In one example, the isocenter of the thoracic cavity can be defined by measuring the width and height of the thoracic cavity in each imaging volume at the approximate height of the aortic valve. The midway point in each dimension of the thoracic cavity is then determined. The vertical axis defined through the body at the intersection of the midpoints in each dimension is used as a rotation axis about which each set of landmark points can be rotated.

Figure 5:
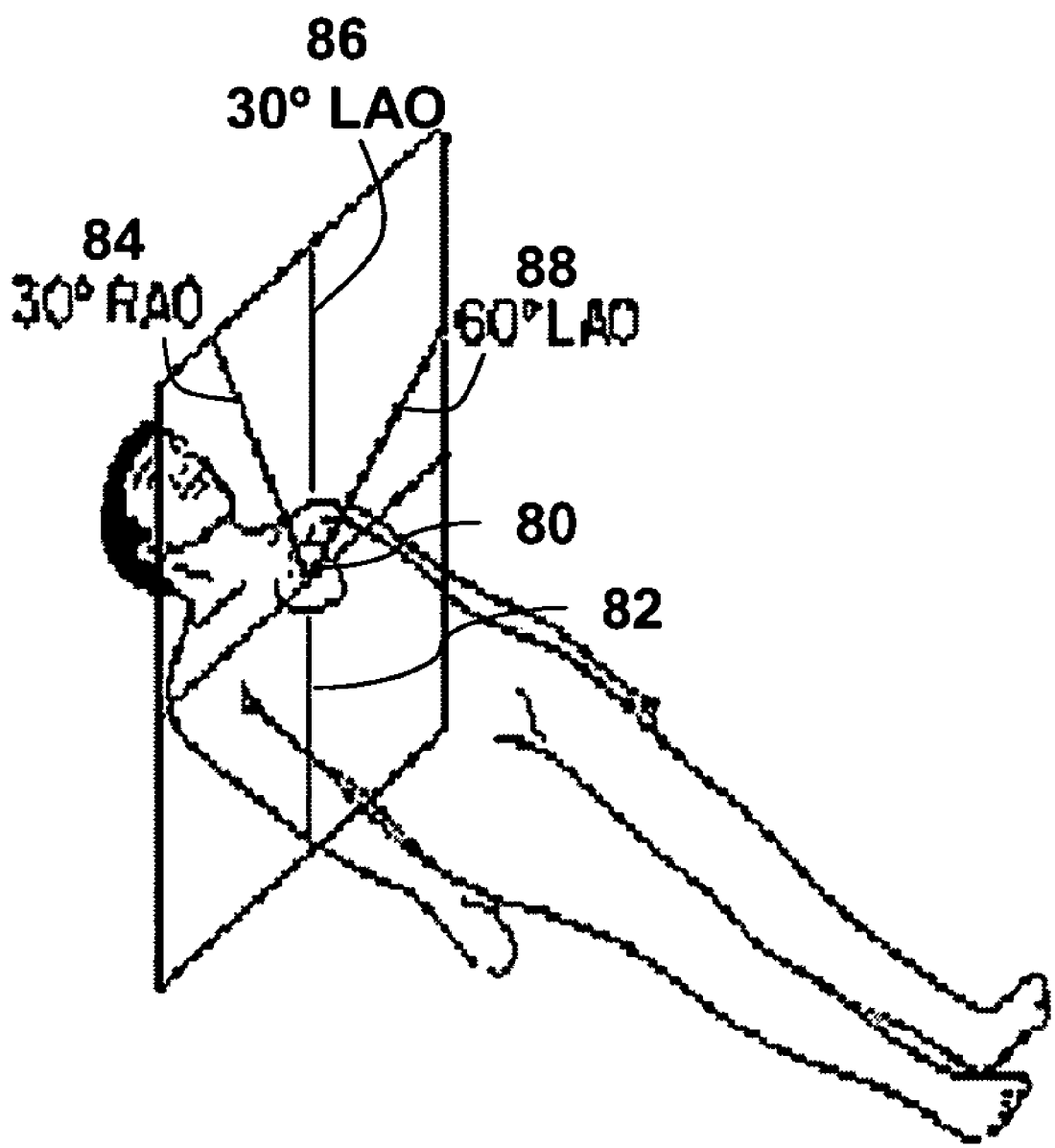
FIG. 5 illustrates an isocenter of a patient's thoracic cavity and the isocenter axis about which a standard C-arm may be rotated for obtaining 2D fluoroscopic views.

FIG. 5 illustrates an isocenter 80 of a patient's thoracic cavity and the isocenter axis 82 about which a standard C-arm may be rotated for obtaining 2D fluoroscopic views. Several rotation angles utilized for fluoroscopic viewing are indicated: 30 degree right anterior oblique angle 84, 30 degree left anterior oblique angle 86, and 60 degree left anterior oblique angle 88.

At step 45 of the flow chart in FIG. 4, the reference and targeted structure landmark point coordinates are rotated about the isocenter axis to project the landmark points on a selected planar view. The selected planar view corresponds to the planar view intended to be used during the surgical procedure for image guidance. Another Matlab code, developed by the inventors and called "CSlocrotation.m", may be used in step 45 to bring together each of the three landmark point coordinates and the isocenter-defining point and allows the user to rotate the landmark points about the isocenter axis to varying angles in either direction.

After these points are rotated around the isocenter axis to a given angle, they are projected onto the selected plane using a parallel projection method at step 50. The resulting 2D landmark point coordinates are then plotted in order to represent how they would appear on the two dimensional image at the given rotation angle. The triangulation parameters calculated at step 60 are the distance ratios and angles determined from a triangle formed by the projected landmark point coordinates in the selected 2D planar view.

Figure 6:
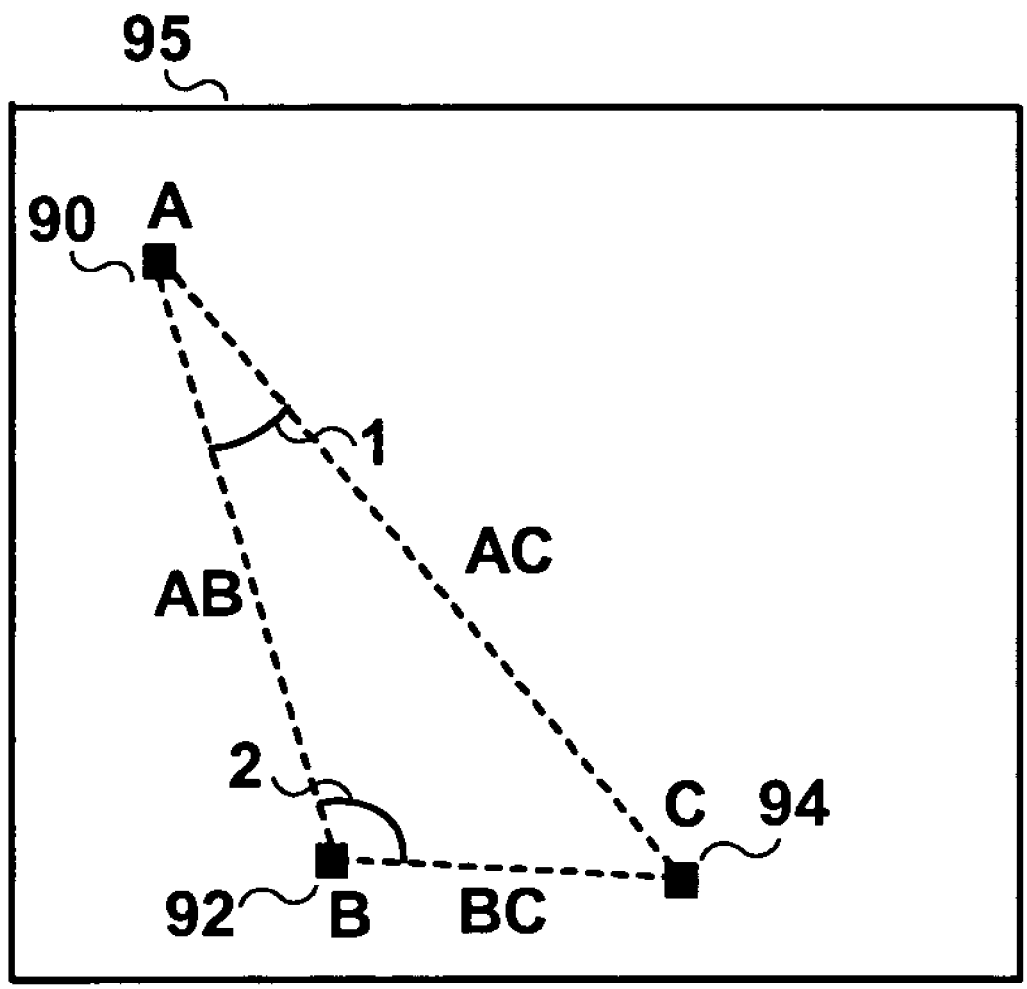
FIG. 6 illustrates triangulation parameters that may be computed from projected landmark point coordinates in a 2D system.

FIG. 6 illustrates triangulation parameters that may be computed from projected landmark point coordinates in a 2D system. If the landmark points described in the example above for localizing the CSos were rotated around the isocenter of the thoracic cavity to a left anterior oblique (LAO) angle of 30°, the projected points may look something like the triangle depicted in FIG. 6. In FIG. 6, a triangle ABC is formed by two projected reference landmark points 90 and 92, labeled A and B respectively, and a projected targeted structure landmark point 94, labeled C, in a selected image plane 95. In the example for localizing the CSos, reference landmark point 90 may correspond to the superior vena cava landmark point, reference landmark point 92 may correspond to the tricuspid valve landmark point 92, and targeted landmark point 94 may correspond to the CSos.

The distances AB, BC, and AC of each respective leg of the triangle ABC formed by the projected landmark points 90, 92 and 94 can be computed from the projected landmark coordinate values. These distances are used to calculate a distance ratio relating the lengths of the sides of the triangle ABC.

Typically two distances will be computed including: 1) the distance from a first reference landmark point to a second reference landmark point and 2) the distance from the first reference landmark point to the targeted landmark point. In the example shown, distance AB, the distance between reference landmark point 90 and the reference landmark point 92, can be computed along with distance AC, the distance between reference landmark point 90 and targeted landmark point 94. The ratio of distance AB to distance AC may then be computed. In other examples, distances AB and BC may be computed to determine a distance ratio. The distance ratio generally relates the distance between two reference landmark points 90 and 92 to the distance between one of the reference landmark points 90 or 92 and the targeted landmark point 94.

In addition to the distance ratio, at least one angle is measured. If the distance ratio is computed using distance AB and distance AC, the angle 1 formed between the vectors AB and AC is computed from the respective landmark point coordinates. If the distance ratio is computed using distance CA and distance CB, the angle 3 formed by these vectors is computed. By knowing a distance ratio and related angle measurement, the location of the targeted structure can be predicted in an intra-operative image containing the reference structures.

Figure 7:
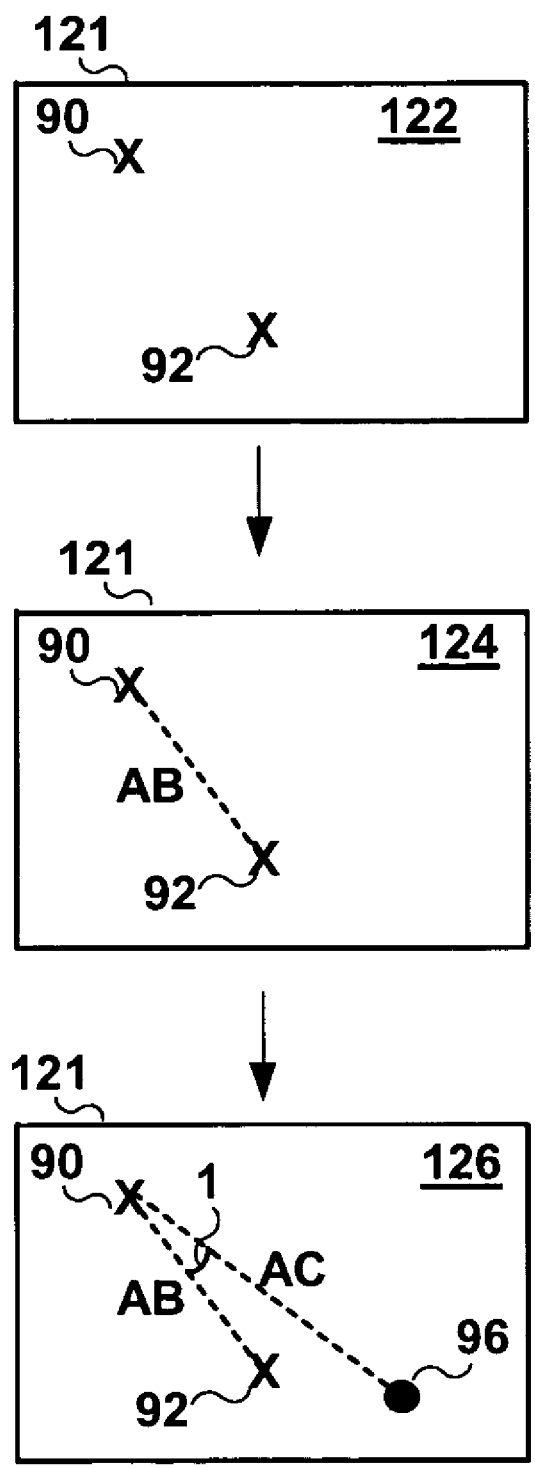
FIG. 7 is a flow diagram illustrating steps included in a method for applying triangulation parameters during an image-guided procedure for plotting a targeted structure on a two-dimensional intra-operative image.

FIG. 7 is a flow diagram illustrating steps included in a method for applying triangulation parameters during an image-guided procedure for plotting a targeted structure on a two-dimensional intra-operative image. In step 120, the location of reference structures 90 and 92 are marked by a user in an intra-operative image frame 121. Image frame 121 is a 2D image in the selected viewing plane. The user may designate the location of reference structures 90 and 92 using a pointing tool, touch screen or other user appliance compatible with the imaging system. A user should attempt to mark the location of each reference structure at a point corresponding to the respective landmark point used in obtaining triangulation data to improve accuracy of the plotted targeted structure location.

After marking the reference structure locations, the distance between the reference structures 90 and 92 in the intra-operative image 121 is measured in step 124. The distance measured corresponds to the distance AB of one leg of the triangle formed by the two reference structures and the targeted structure as illustrated in FIG. 6. The distance AB may be measured in any units since unitless distance ratios will be applied to estimate the location of the targeted structure.

In step 126, triangulation parameters are applied to plot the estimated location 96 of the targeted structure. In one embodiment, using the labeling convention of FIG. 6, the measured distance AB in image frame 101 is multiplied by the distance ratio AC:AB to determine the distance AC between reference structure 90 and the targeted structure. A point 96 is then plotted at a distance AC from reference structure 90 along a vector extending at an angle 1 from the side AB extending. Plotted point 96 provides a target for the clinician to guide an instrument toward during the invasive procedure. An area or perimeter surrounding the plotted point 96 may be shaded or outlined to indicate inherent error or variability in the triangulation parameters.

The example described above for localizing the CSos may be used to further describe how one might apply mean triangulation parameters in a clinical setting. Triangulation parameters may be obtained from a number of subjects from a selected patient population relating the location of the targeted CSos and SVC and TV reference structures. An assumption may be made that, from a given population of patients, there is a low variability in the distance ratio between a SVC-TV leg and a SVC-CSos leg and an angle between the SVC-TV and SVC-CSos legs of the triangle in the LAO 30 degree perspective (as illustrated in FIG. 5).

During a procedure requiring cannulation of the CSos, a physician would orient a fluoroscopy C-arm to view a patient's heart from an LAO 30 rotation angle and then, using a catheter, the physician would locate the SVC ostium and the TV annulus center point, marking these locations on the fluoroscopic view. These points may be manually marked on the monitor displaying the fluoroscopic image or electronically marked on the image via a software package, likewise the distance between these points on the fluoroscopic view could be measured using a ruler and a line drawn between the two points or calculated by the software package. Then, using the previously generated triangulation parameter database on the selected patient population, the length of the SVC-CSos leg of the triangle would be calculated using the distance ratio measurement between the SVC-TV and SVC-CSos legs of the triangle. The trajectory of the SVC-CSos leg of the triangle would then be defined by using the existing line on the fluoroscopic view (SVC-TV leg) and the angle measurement already defined from the triangulation parameter database.

After plotting on the fluoroscopic screen a point corresponding to the predicted location of the CSos, resulting from the length and trajectory calculations, a perimeter based on variability found in the population would be drawn about the predicted CSos location providing a targeted to guide the physician in cannulating the coronary sinus. If the patient-specific method of localization is used, the physician can follow the same steps as those outlined above for the population-based tool, the only difference being a smaller target since patient population variability does not come into play.

Figure 8:
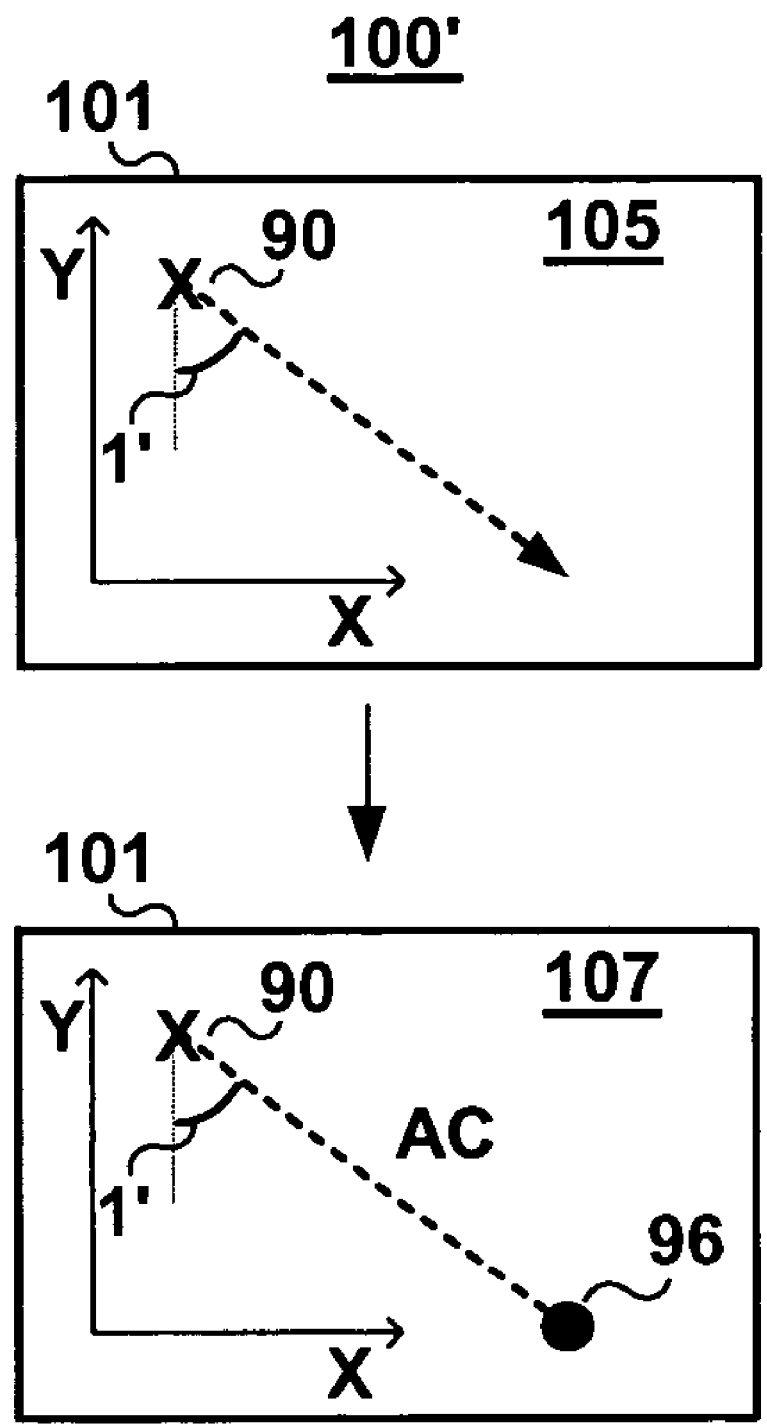
FIG. 8 is an illustration summarizing steps included in yet another embodiment of the present invention wherein localization parameters determined from one reference structure and a local coordinate system are used in plotting a targeted structure location in an intra-operative image.

FIG. 8 is an illustration summarizing steps included in yet another embodiment of the present invention wherein localization parameters determined from one reference structure and a local coordinate system are used in plotting a targeted structure location in an intra-operative image. In some applications, a single reference structure 90 may be selected. In a data acquisition method performed prior to a surgical procedure, the distance between the reference structure landmark point and the targeted landmark point is measured. The angle between a local coordinate axis and the trajectory extending between the reference landmark point in the direction of the targeted landmark point is determined. The local coordinate axes are defined relative to the imaging area 121. This distance measurement and angle are used in a method for plotting the estimated target structure location during an image-guided procedure.

As shown in FIG. 8, the location of the reference structure 90 in a two dimensional intra-operative image 121 is marked by a clinician in step 125. A trajectory is generated extending from reference point 90 at an angle 1' from an axis, in this example the Y axis, of a local coordinate system. In step 107, targeted point 96 is plotted along the trajectory at the distance AC from reference point 90. Distance AC corresponds to the distance measured during data acquisition between the reference point 90 and the targeted landmark point. Thus, in some applications, a targeted point location may be plotted using a minimum of one reference structure and a defined local coordinate system. The localization parameter data includes an absolute distance measurement rather than a distance ratio.

The methods described herein may be applied in a stepwise manner for locating a sequence of structures. For example, in a procedure for placing a catheter or lead in a cardiac vein, the methods described herein may be applied to first localize the coronary sinus ostium. Once the coronary sinus ostium is located, it may be used as a reference structure for locating a targeted cardiac vein. Triangulation parameters may be obtained relating the location of the CSos and a second reference structure, for example, the bicuspid valve, for localizing the targeted cardiac vein. Thus a targeted structure in a first localization step may be used as a reference structure in a second localization step performed to ultimately guide an instrument to a final therapy delivery or diagnostic site.

Thus a method has been described for plotting a targeted structure location on intra-operative images based on previously determined triangulation parameters. The methods provided by the present invention can be used in any intervention requiring precise structure localization using 2D or 3D imaging systems. Procedures in which the present invention may be useful include, but are not limited to, CSos cannulation, pacing lead placement, local delivery of drugs, biologic or genetic material, tissue ablation, percutaneous valve placement, and placement of physiological sensors. The use of the present invention to aid a clinician in localizing a targeted structure can reduce procedure time, decrease radiation exposure by requiring fewer fluoroscopic images, and result in a more predictable therapy result. The use of the localization method can increase physician confidence in performing a particular procedure and reduce the physician training time required for learning the procedure. The methods described herein are intended to illustrate exemplary methods for practicing the invention and are not intended to be limiting with regard to the following claims.

What is claimed is:

1. A method, comprising:

generating a three dimensional image of a body portion including a targeted structure for a surgical procedure;

selecting reference structures located in the generated three dimensional image;

calculating landmark point coordinates for defining locations of each of the targeted structure and the reference structures to generate respective targeted structure landmark point coordinates and reference structures landmark point coordinates;

computing triangulation parameters relating the location of the targeted structure landmark point coordinates to the reference structures landmark point coordinates, wherein the computed triangulation parameters include a distance ratio and an angle, wherein the distance ratio relates the lengths of two sides of a triangle formed by the targeted structure landmark point coordinates and two landmark point coordinates of the reference structures landmark point coordinates and the angle is the angle formed between the two sides of the triangle;

acquiring an intra-operative three dimensional image during the surgical procedure;

identifying locations of the reference structures in the intra-operative image; and plotting a location of the targeted structure on the intra-operative image in response to the computed triangulation parameters and the identified locations of the reference structures in the intra-operative image.

2. The method of claim 1, wherein calculating the landmark point coordinates comprises:

generating separate oblique planes through each of the targeted reference structure and the selected reference structures;

selecting a plurality of points corresponding to one of the targeted structure and the reference structure in each of the respective oblique planes; and calculating the landmark point coordinates in response to the selected plurality of points.

3. The method of claim 2, wherein the selected plurality of points corresponding to one of the targeted structure and the reference structures in each of the respective oblique planes are structure boundary points.

4. The method of claim 2, wherein the selected plurality of points corresponding to one of the targeted structure and the reference structures in each of the respective oblique planes are selected automatically based on a gray-scale or color-scale change in a digitized image.

5. The method of claim 2, wherein the selected plurality of points corresponding to one of the targeted structure and the reference structures in each of the respective oblique planes are selected manually using a pointing tool.

6. The method of claim 2, wherein one of the targeted structure landmark point coordinates and the reference structures landmark point coordinates are the coordinates of a centroid calculated from the selected plurality of points.

7. The method of claim 1, wherein computing triangulation parameters comprises computing triangulation parameters corresponding to each of two or more triangles, the two or more triangles being formed by the targeted structure landmark point coordinates and two of the reference structure landmark point coordinates.

8. The method of claim 7, wherein plotting the location of a targeted structure in an intra-operative image comprises:

generating a first circle defined by rotating a trajectory extending from a first identified reference structure at a corresponding computed angle relative to a line segment defined by the first identified reference structure and a second identified reference structure, the circumference of the circle being a distance from the first identified reference structure, wherein the distance is determined from the corresponding computed distance ratio and a distance measured in the intra-operative image between the first identified reference structure and the second reference structure;

generating a second circle by rotating a trajectory extending from a third identified reference structure at a corresponding computed angle relative to a line segment defined by the third identified reference structure and the second identified reference structure, the circumference of the circle being a distance from the third identified reference structure determined from the corresponding computed distance ratio and a distance measured in the intra-operative image between the third identified reference structure and the second identified reference structure; and plotting the location of the targeted structure at an intersection of the first circle and the second circle.

9. The method of claim 1, wherein the reference structures include the superior vena cava ostium and the tricuspid valve.

10. The method of claim 1, wherein the targeted structure is the coronary sinus ostium.

11. The method of claim 1, wherein the targeted structure is a cardiac vein.

12. The method of claim 1, wherein the targeted structure is a targeted pacing site.

13. The method of claim 1, further including using electrophysiological mapping for locating a targeted structure or selected reference structures.

14. A method, comprising:

generating a three dimensional image of a body portion including a targeted structure for a surgical procedure;

selecting reference structures included in the image;

calculating landmark point coordinates for defining the locations of each of the targeted structure and the reference structures to generate respective targeted structure landmark point coordinates and reference structures landmark point coordinates;

defining an isocenter axis location in the patient's body about which a two-dimensional imaging plane is rotated;

rotating the targeted structure landmark point coordinates and the reference structures landmark point coordinates about the isocenter axis to a selected planar imaging view;

calculating the targeted structure landmark point coordinates and the reference structures landmark point coordinates projected onto the selected planar view;

computing triangulation parameters relating the location of the projected targeted structure landmark point coordinates to the projected reference structures landmark point coordinates, wherein the computed triangulation parameters include a distance ratio and an angle, wherein the distance ratio relates the lengths of two sides of a triangle formed by the targeted structure landmark point coordinates and two reference structure landmark points of the reference structures landmark point coordinates and the angle is the angle formed between the two sides of the triangle;

acquiring an intra-operative two-dimensional image during the surgical procedure;

identifying the locations of the selected reference structures in the intra-operative image; and plotting a location of the targeted structure on the intra-operative image in response to the computed triangulation parameters and the identified locations of the reference structures in the intra-operative image.

15. The method of claim 14, wherein calculating the landmark point coordinates comprises:
generating separate oblique planes through each of the targeted structure landmark point coordinates and selected reference structures;
selecting a plurality of points corresponding to one of the targeted structure and the reference structure in each of the respective oblique planes; and
calculating the landmark point coordinates in response to the plurality of selected points.

16. The method of claim 15, wherein selected plurality of points corresponding to one of the targeted structure and the reference structures in each of the respective oblique planes are structure boundary points.

17. The method of claim 15, wherein the selected plurality of points corresponding to one of the targeted structure and the reference structures in each of the respective oblique planes are selected automatically based on a gray-scale or color-scale change in a digitized image.

18. The method of claim 15, wherein the selected plurality of points corresponding to one of the targeted structure and the reference structures in each of the respective oblique planes are selected manually using a pointing tool.

19. The method of claim 15, wherein the targeted structure landmark point coordinates and the reference structures landmark point coordinates are the coordinates of a centroid calculated from the selected plurality of points.

20. The method of claim 14, wherein plotting the location of a targeted structure in an intra-operative image comprises:
measuring the distance between two identified reference structures;
extending a trajectory from a first identified reference structure at a corresponding computed angle relative to a line segment defined by the first identified reference structure and a second identified reference structure; and
plotting the targeted structure at a location on the trajectory a distance from the first identified reference structure, wherein the distance is determined in response to the corresponding computed distance ratio and a distance measured in the intra-operative image between the first identified reference structure and the second identified reference structure.

21. The method of claim 14, wherein the first identified reference structure and the second identified reference structure include the superior vena cava ostium and the tricuspid valve.

22. The method of claim 14, wherein the targeted structure is the coronary sinus ostium.

23. The method of claim 14, wherein the targeted structure is a cardiac vein.

24. The method of claim 14, wherein the targeted structure is a targeted pacing site.

25. The method of claim 14, further comprising locating one of the targeted structure and the reference structures using electrophysiological mapping.

* * * * *